United States Patent
Dobak, III et al.

(10) Patent No.: US 6,193,644 B1
(45) Date of Patent: *Feb. 27, 2001

(54) CRYOSURGICAL PROBE WITH SHEATH

(75) Inventors: John D. Dobak, III; Kambiz Ghaerzadeh; Xiaoyu Yu, all of San Diego, CA (US)

(73) Assignee: CryoGen, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/262,588

(22) Filed: Mar. 4, 1999

Related U.S. Application Data

(63) Continuation of application No. 08/774,148, filed on Dec. 26, 1996, now Pat. No. 5,910,104.

(51) Int. Cl.$^7$ .................................................. A61F 5/58

(52) U.S. Cl. ............................................. 600/23; 606/121

(58) Field of Search ..................................... 600/121, 122, 600/123, 124, 125; 606/20–26; 607/96; 604/263

(56) References Cited

U.S. PATENT DOCUMENTS

| 2,319,542 | 5/1943 | Hall . |
| 2,672,032 | 3/1954 | Towse .................................. 62/126 |
| 3,272,203 | 9/1966 | Chato . |

(List continued on next page.)

FOREIGN PATENT DOCUMENTS

| 0 271 989 | 11/1990 | (EP) . |
| 1465540 | 1/1967 | (FR) . |
| 1468862 | 1/1967 | (FR) . |

(List continued on next page.)

OTHER PUBLICATIONS

Military & Commercial Applications for Low Cost Cryocoolers, Electronic Industries Assoc. Cryelectronics Division (Jan. 31 and Feb. 1, 1996).

Harly, S. et al., Heat Exchange in the Cryosurgery of Meniere's Disease; Experimental and Clinical Studies, 14 Cryobiology 609–613 (1977).

File History of U.S. Pat. 5,758,505 Patent.

(List continued on next page.)

*Primary Examiner*—Linda C. M. Dvorak
*Assistant Examiner*—R. Kearney
(74) *Attorney, Agent, or Firm*—Gerald W. Spinks

(57) ABSTRACT

A sheath for use on a closed loop Joule-Thomson cryosurgical probe, and the combination of the and the closed loop probe. The sheath is slipped over the probe, thereby separating the probe from the environment. The sheath has a grip which fits over the handle of the cryosurgical probe, and an extendible shroud which can be longitudinally extended to cover tubing and which are attached to the handle. The sheath has a hollow multi-lumen catheter shaped and sized to fit snugly over the cannula of the cryosurgical probe. The catheter is not thermally conductive, preventing transfer of heat from the ambient to the gas mixture, and preventing the freezing of tissues at undesired locations along the catheter. A thermally conductive cap or tip is attached to the distal end of the hollow catheter. The thermally conductive cap or tip fits snugly over the cold tip on the probe, and it efficiently transfers heat from the target tissue to the cold tip, which in turn transfers heat to the expanded gas mixture. Various forms of auxiliary instrumentation can be mounted on the catheter or conductive tip, such as a temperature sensor, a heater, an ultrasonic transducer, or an optical element of a viewing, illumination, or laser system. Connections between the instrumentation near the distal end of the catheter and the probe are made via a plurality of lumens passing longitudinally through the wall of the catheter.

11 Claims, 8 Drawing Sheets

U.S. PATENT DOCUMENTS

| | | | |
|---|---|---|---|
| 3,273,356 | 9/1966 | Hoffman | 62/514 |
| 3,298,371 | 1/1967 | Lee . | |
| 3,368,549 | 2/1968 | Armao . | |
| 3,398,738 | 8/1968 | Lamb et al. . | |
| 3,401,533 | 9/1968 | Maybury | 62/54 |
| 3,431,750 | 3/1969 | LeFranc | 62/514 |
| 3,439,680 | 4/1969 | Thomas . | |
| 3,477,434 | 11/1969 | Hood, Jr. et al. . | |
| 3,536,075 | 10/1970 | Thomas, Jr. . | |
| 3,613,689 | 10/1971 | Crump et al. . | |
| 3,630,203 | 12/1971 | Sellinger et al. . | |
| 3,662,755 | 5/1972 | Rautenbauch et al. . | |
| 3,696,813 | 10/1972 | Wallach . | |
| 3,729,945 | 5/1973 | Linnett | 62/40 |
| 3,750,417 | 8/1973 | Johannes, et al. | 62/114 |
| 3,768,273 | 10/1973 | Missimer | 62/84 |
| 3,786,814 | 1/1974 | Armao . | |
| 3,827,436 | 8/1974 | Stumpf et al. . | |
| 3,889,680 | 6/1975 | Armao . | |
| 3,913,581 | 10/1975 | Ritson et al. . | |
| 3,924,628 | 12/1975 | Droegemueller et al. . | |
| 3,932,154 | 1/1976 | Coers et al. | 62/9 |
| 3,971,383 | 7/1976 | van Gerven . | |
| 4,015,606 | 4/1977 | Mitchiner et al. . | |
| 4,206,609 | 6/1980 | Durenec | 62/6 |
| 4,207,897 | 6/1980 | Lloyd et al. . | |
| 4,211,231 | 7/1980 | Rzasa . | |
| 4,275,734 | 6/1981 | Mitchiner . | |
| 4,377,168 | 3/1983 | Rzasa et al. . | |
| 4,601,296 | 7/1986 | Yerushaimi . | |
| 4,646,722 | 3/1987 | Silverstein et al. . | |
| 4,781,033 | 11/1988 | Steyert et al. | 62/514 |
| 4,809,678 | 3/1989 | Klein . | |
| 4,829,785 | 5/1989 | Hersey | 62/467 |
| 4,840,043 | 6/1989 | Sakitani et al. | 62/51.2 |
| 4,875,346 | 10/1989 | Jones et al. | 62/467 |
| 4,878,485 | 11/1989 | Adair . | |
| 4,990,412 | 2/1991 | Hersey | 429/8 |
| 5,061,246 | 10/1991 | Anapliotis | 604/171 |
| 5,063,747 | 11/1991 | Jones et al. | 62/461 |
| 5,077,979 | 1/1992 | Skertic et al. | 62/51.2 |
| 5,078,713 | 1/1992 | Varney | 606/23 |
| 5,101,894 | 4/1992 | Hendricks | 165/164 |
| 5,139,496 | 8/1992 | Hed | 606/23 |
| 5,147,355 | 9/1992 | Friedman et al. | 606/23 |
| 5,150,579 | 9/1992 | Hingst | 62/51.2 |
| 5,157,938 | 10/1992 | Bard et al. | 62/335 |
| 5,193,349 | 3/1993 | Laverman et al. | 62/64 |
| 5,237,984 | 8/1993 | Williams, III et al. . | |
| 5,275,595 | 1/1994 | Dobak, III | 606/23 |
| 5,281,212 | 1/1994 | Savage et al. | 606/15 |
| 5,281,213 | 1/1994 | Milder et al. | 606/15 |
| 5,281,215 | 1/1994 | Milder | 606/20 |
| 5,281,217 | 1/1994 | Edwards et al. | 606/41 |
| 5,301,657 | 4/1994 | Lafferty et al. . | |
| 5,324,286 | 6/1994 | Fowle | 606/23 |
| 5,334,181 | 8/1994 | Rubinsky et al. | 606/22 |
| 5,337,572 | 8/1994 | Longsworth | 62/51.2 |
| 5,365,750 | 11/1994 | Greenthal | 62/293 |
| 5,402,768 | 4/1995 | Adair . | |
| 5,403,309 | 4/1995 | Coleman et al. | 606/20 |
| 5,408,992 | 4/1995 | Hamlin et al. . | |
| 5,423,807 | 6/1995 | Milder | 606/20 |
| 5,476,090 | 12/1995 | Kishi | 600/121 |
| 5,522,870 | 6/1996 | Ben-Zion | 607/104 |
| 5,573,532 | 11/1996 | Chang et al. | 606/26 |
| 5,595,065 | 1/1997 | Boiarski et al. | 62/222 |
| 5,617,739 | 4/1997 | Little | 62/69 |
| 5,624,392 | 4/1997 | Saab | 604/43 |
| 5,644,502 | 7/1997 | Little | 364/496 |
| 5,674,218 | 10/1997 | Rubinsky et al. | 606/20 |
| 5,690,605 | 11/1997 | Hamlin et al. | 600/109 |
| 5,724,832 | 3/1998 | Little et al. | 62/613 |

FOREIGN PATENT DOCUMENTS

| | | |
|---|---|---|
| 2 482 445 | 3/1980 | (FR) . |
| 2477406 | 9/1981 | (FR) . |
| 1 336 892 | 11/1973 | (GB) . |
| 2 026 324 | 2/1980 | (GB) . |
| 2 080 117 | 2/1982 | (GB) . |
| 2 093 964 | 9/1982 | (GB) . |
| 2 283 678 | 5/1995 | (GB) . |
| 2 289 412 | 11/1995 | (GB) . |
| 2 289 413 | 11/1995 | (GB) . |
| 2 289 414 | 11/1995 | (GB) . |
| 2 289 510 | 11/1995 | (GB) . |
| 57-126430 | 8/1982 | (JP) . |
| 333857 | 4/1974 | (SU) . |
| 333858 | 4/1974 | (SU) . |
| 527467 | 9/1976 | (SU) . |
| 534484 | 11/1976 | (SU) . |
| 565052 | 7/1977 | (SU) . |
| 573496 | 9/1977 | (SU) . |
| 627154 | 8/1978 | (SU) . |
| 637417 | 12/1978 | (SU) . |
| 676604 | 7/1979 | (SU) . |
| 768795 | 10/1980 | (SU) . |
| 802348 | 2/1981 | (SU) . |
| 802349 | 2/1981 | (SU) . |
| 802350 | 2/1981 | (SU) . |
| 802351 | 2/1981 | (SU) . |
| 832268 | 5/1981 | (SU) . |
| 839516 | 6/1981 | (SU) . |
| 918298 | 4/1982 | (SU) . |
| 966107 | 10/1982 | (SU) . |
| 1054400 | 1/1983 | (SU) . |
| 1026795 | 7/1983 | (SU) . |
| 1026796 | 7/1983 | (SU) . |
| 1089099 | 4/1984 | (SU) . |
| 1090699 | 5/1984 | (SU) . |
| 1134856 | 1/1985 | (SU) . |
| 1158567 | 5/1985 | (SU) . |
| 1189434 | 11/1985 | (SU) . |
| 1437012 | 11/1988 | (SU) . |
| 1774140 | 11/1992 | (SU) . |
| WO93/04647 | 3/1993 | (WO) . |
| WO 93/08753 | 5/1993 | (WO) . |
| WO 95/13025 | 5/1995 | (WO) . |
| WO 95/30379 | 11/1995 | (WO) . |
| WO 95/30380 | 11/1995 | (WO) . |

OTHER PUBLICATIONS

Cryogen Documents, Bates No. CRY 000428– CRY 000479.

Little, W.A., Handwritten Notes to Valley Laboratories, Bates Nos. M00001–M00009 (Apr. 1987).

Answer, Affirmative Defenses, and Counterclaims of Defendant Johnson & Johnson to CryoGen's First Amended Complaint for Infringement of U.S. Pat. Nos. 5,758,505 & 5,910,104 *Cryogen Inc. v. Johnson and Johnson, Inc.*, Case No. C–99–02471 VRW (N.D.Cal. Aug. 31, 1999).

Answer, Affirmative Defenses, and Counterclaims of Defendants FemRx and Ethicon to CryoGen's First Amended Complaint for Infringement of U.S. Pat. Nos. 5,758,505 & 5,910,104 *Cryogen Inc. v. Johnson and Johnson, Inc.*, Case No. C–99–02471 VRW (N.D.Cal. Aug. 31, 1999).

Answer, Affirmative Defenses, and Counterclaims of Defendant and Counterclaimant MMR Technologies, Inc. to CryoGen's First Amended Complaint for Infringement of U.S. Pat. Nos. 5,758,505 & 5,910,104, *Cryogen Inc. v. Johnson and Johnson, Inc.*, Case No. C–99–02471 VRW (N.D.Cal. Aug. 31, 1999).

Supplemental Responses and Objections of FemRX, Inc., Ethicon, Inc., and Johnson & Johnson to CryoGen, Inc.'s Second Set of Interrogatories, *Cryogen Inc. v. Johnson and Johnson, Inc.*, Case No. C–99–02471 VRW (N.D.Cal. Aug. 31, 1999), at 4–7.

EPO Opposition to European Patent No. 0584930, FE0701836–701875.

Deposition of Gerald W. Spinks, Esq. of Spinks Law Firm ("Spinks Dep."): 57–147, 148–233, 246–275, 275–325, (filed under M.P.E.P. Sec. 724.02).

Docket Sheet (updated Mar. 30, 2000), *Cryogen Inc. v. Johnson and Johnson, Inc.*, Case No. C–99–02471 VRW (N.D.Cal., filed May 25, 1999).

Docket Sheet (updated Mar. 30, 2000), *FemRx, Inc. v. CryoGen, Inc.*, Case No. C98–02330 VRW (N.C. Cal. Filed Jun. 8, 1998).

Abstract 907,054; A.V. Mostitskiy.

S. Bard, A Two–Stage 80 K/140 K Sprption Cryocooler, Proceedinngs of the 12th International Cryogenic Engineering Conference, p. 626–630. (R.G. Scurlock and C.A. Bailey, eds.) Butterworth, Guilford, UK 1988).

J. Baust; Underlying Mechanism of Damage and New Concepts in Bryosurgery, Cryosurgery: Mechanisms and Applications, p. 21–36 (International Institute of Refrigeration, Paris 1995).

E. Bodio, The application of Multicomponent Gaseous Mixtures in Linde–Hampson Coolers, Wroclaw Institute of Tech. (1985); Partial translation to English.

V. M. Brojanski; Developments in Cryotechnology to 2000; May 1989; pp. 193–195; 16th Cryotechnology Congress; Translated to English.

Z. Chang; Optimization of Cryosurgical Instrumentation for Use in Minimally Invasive Prostate Surgery; 1993; pp. 45–55; Recent Advances in Cryogenic Engineering.

W. Bald; Cryogenic Surgery; pp. 1383–1434, Reports on Progress in Physics; date unknown.

W. Droegemueller; Cryocoagulation of the Endometrium at the Uterine Cornua; May 1978; pp. A58–A66; American Journal of Obstetrics and Gynecology.

A. Gage; Cryosurgery; date unknown; pp. 893–908; Encyclopedia of Medical Devices and Instrumentation.

G. Garamy; Engineering Aspects of Cryosurgical Instruments Employing Liquid Nitrogen; 1967; pp. 283–308; International Ophthalmology Clinics.

J. Jones; Mixed Gas Sorption Joule–Thomson Refrigerator; May 1991; pp. i, 1–4, NASA Tech Brief.

J. Jones; Sorption Refrigeration Research at JPL/NASA; 1992; pp. 143–152; International Institute of Refrigeration.

J. Dow; The Functional Anatomy of Urologic Cryosurgical Unit and Its Relation to the Technique, Complications, and Results of Cryosurgery of the Prostate; Oct. 1969; pp. 572–577; The Journal of Urology, vol. 104.

J. Edwards; A Simple Cryosurgical Instrument and Its Application in Ethiopia; Nov. 1966; pp. 415–422; British Journal of Ophthalmology.

D. Ferris; Cryosurgical Equipment: A Critical Review; Feb. 1992; pp. 185–193; The Journal of Family Practice, vol. 35, No. 2.

W. Little; Microminiature Refrigeration; Jun. 1983; pp. 661–680; Rev. Sci. Instrum., vol. 55 No. 5.

W. Little; Advances in Joule–Thomson Cooling; 1990; pp. 1305–1314; Advances in Cryogenic Engineering, vol. 35.

S. Amoils; The Joule–Thomson Cryoprobe; Jan. 1967; pp. 201–207; Arch. Ophthal., vol. 78.

D. Friend; Thermophysical Property Computer Packages from NIST; 1992; pp. 13–18; ASME HTD vol. 225.

A. Gage; Current Progress in Cryosurgery; Mar. 1988; pp. 483–486; Cryobiology, vol. 25.

D. Hill; Throttle Cycle Cooler Vibration Characterization; 5 pages; date and place of publication unknown.

A. Khatri; A Throttle Cycle Refrigerator Operating below 77K; 8 pages; date and place of publication unknown.

G. Venkatarathnam; Matrix Heat Exchangers and Their Application in Cryogenic Systems; Dec. 1989; pp. 907–918; Cryogenics, vol. 30.

R. Hubbell; New Heat Transfer and Friction Factor Design Data for Perforated Plate Heat Exchangers; 1988; pp. 383–390; Advanced Cryogenic Engineering, vol. 33.

H. Jichuan; Heat Transfer Characteristics of a Perforated Plate; Sep. 1990; pp. 318–322; Cryogenics, vol. 30.

G. Venkatarathnam; Heat Transfer and Flow Friction Correlations in Perforated Plate Matrix Heat Exchangers; Sep. 1990; pp. 313–317; Cryogenics, vol. 30.

Z. Chang; Development of a High–Performance Multiprobe Cryosurgical Device; Sep. 1994; pp. 383–390; Biomedical Instrumentation and Technology, vol. 28.

A. Hamilton; An Electronic Cryoprobe for Cryosurgery Using Heat Pipes and Thermoelectric Coolers; May 1993; pp. 104–109; Journal of Medical Engineering and Technology, vol. 17, No. 3.

Author unknown; Technical Support Package on Mixed Gas Sorption Joule–Thomson Refrigerator; May 1991; Jet Propulsion Lab.

A. Kleemenko; One Flow Cascade Cycle(In Schemes of Natural Gas Liquefaction and Separation); 1959; pp. 34–39; Proceedings of International Congress of Refrigeration.

V. Kobryanskiy; A Cryomedical Device Based On A Closed Cycle Joule–Thomson Cooling System; Mar. 1978; pp. 71–72; place of publication unknown—Translated to English.

W. Little; Development of a Low Cost, Cryogenic Refrigeration Systems for Cooling of Cryoelectronics; 1994; pp. 1467–1474; Advances in Cryogenic Engineering, vol. 39.

W. Little; Microminiature Refrigerators for Joule–Thomson Cooling of Electronic Chips and Devices; 1990; pp. 1325–1333; Advances in Cryogenic Engineering, vol. 35.

W. Little; Recent Developments in Joule–Thomson Cooling: Gases, Coolers and Compressors; 9 pages; date and place of publication unknown.

W. Porter; Processor Performance Enhancement Using CPU Sub–Cooling; 1994; pp. 242–246; Proceedings of the International Electronic Packaging Conference.

Y. Rabin; Compact Cryosurgical Apparatus for Minimally Invasive Procedures; May 1997; pp. 251–258; Biomedical Instrumentation and Technology.

S. Sood; Prediction Methods for Vapor–Liquid Equilibria in Multi–Component Cryogenic Mixtures; Jun. 1970; pp. 199–207; Cryogenics.

D. Torre; Alternate Cryogens for Cryosurgery; Jun. 1975; pp. 56–58; Journal of Dermatology Surgery.

A. Gassanov; Experience with the Development and Use of Cryogenic Surgical Equipment; Sep. 1986; pp. 41–42; place of publication unknown—Translated to English.

A. Grokholski; The Krioelektronika–1 Cryogenic Dental Unit; Sep. 1981; pp. 16–20; Meditsinskaya Tekhnika—Translated to English.

J. Jones; Cryogenic Mixed Fluid Application Study and Computer Code Development; pp. i–iv, 1–18; date and place of publication unknown.

J. Pollard; The Use of Crygoens in Glaucoma; Nov. 1965; pp. 553–556; Southern Medical Journal.

S. Amoils; A Cryosurgical System for Retinal Detachments and Tumours; Feb. 1969; pp. 188–190; South African Medical Journal.

J. Addonizio; Another Look at Cryoprostatectomy; Dec. 1981; pp. 223–227; Cryobiology, vol. 19.

F. Brown; Office Gynecologic Procedures; Sep. 1986; pp. 493–511; Primary Care, vol. 13.

J. Baust; Minimally Invasive Cryosurgery—Technological Advances; Oct. 1996; pp. 373–384; Cryobiology, vol. 34.

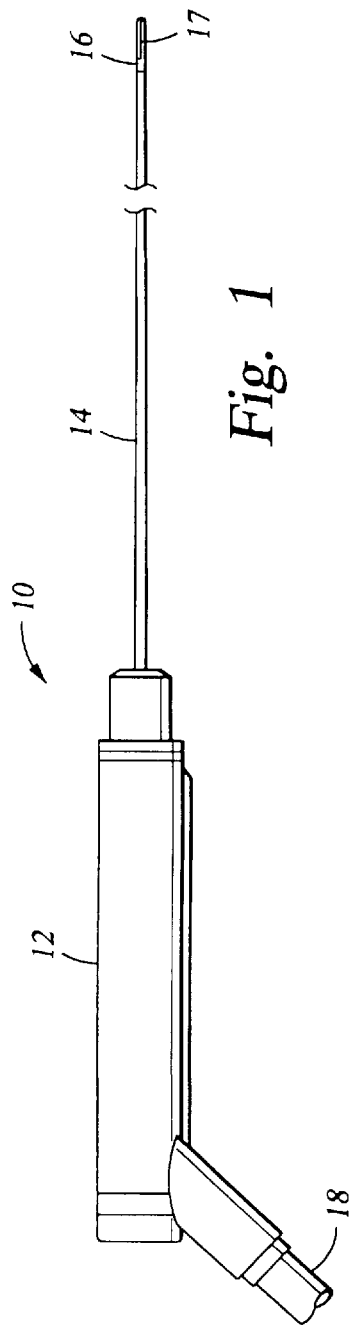
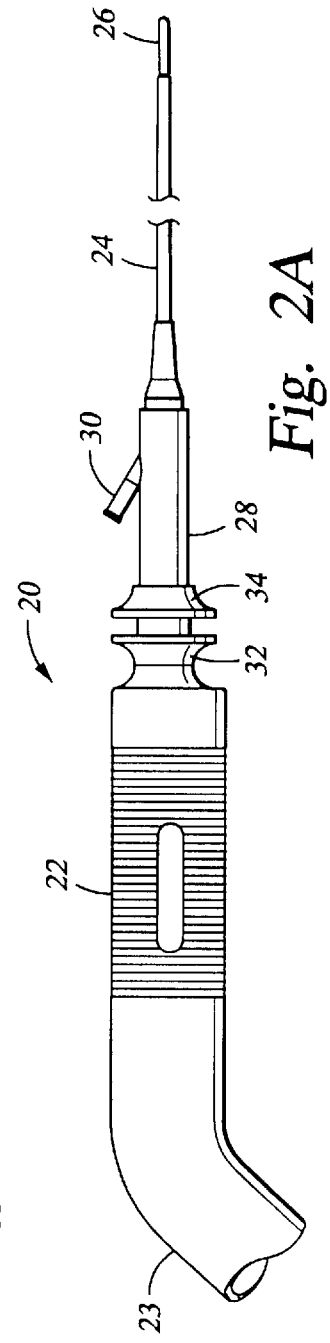
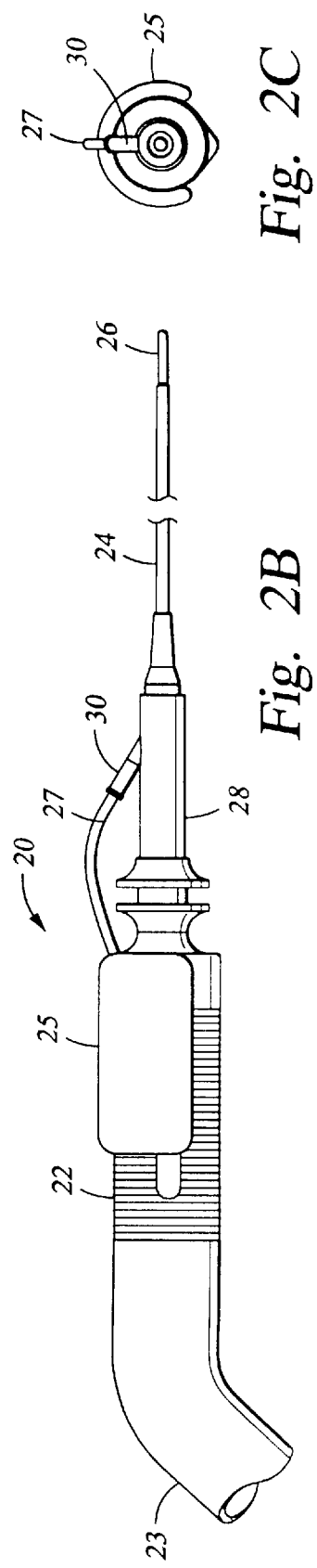

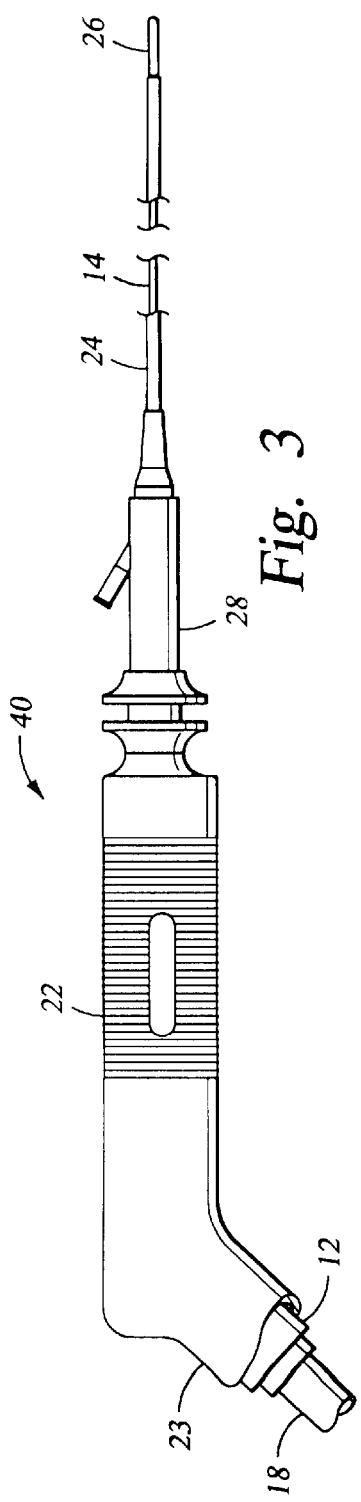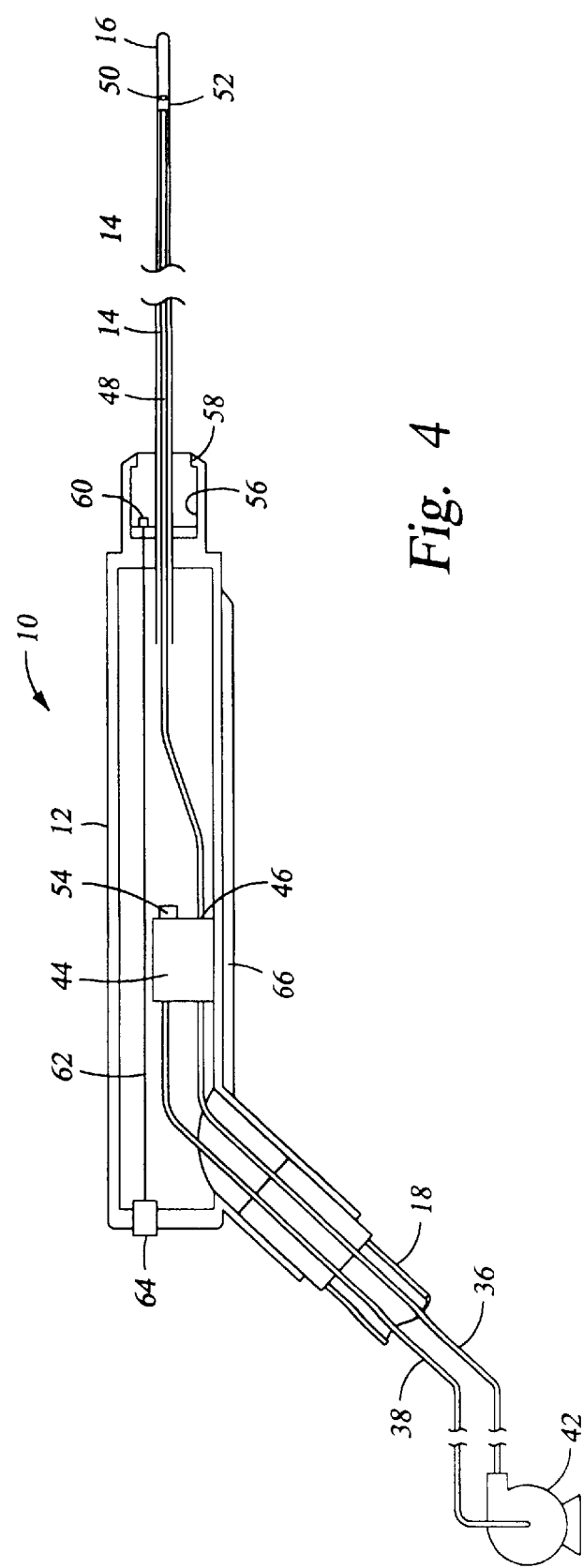

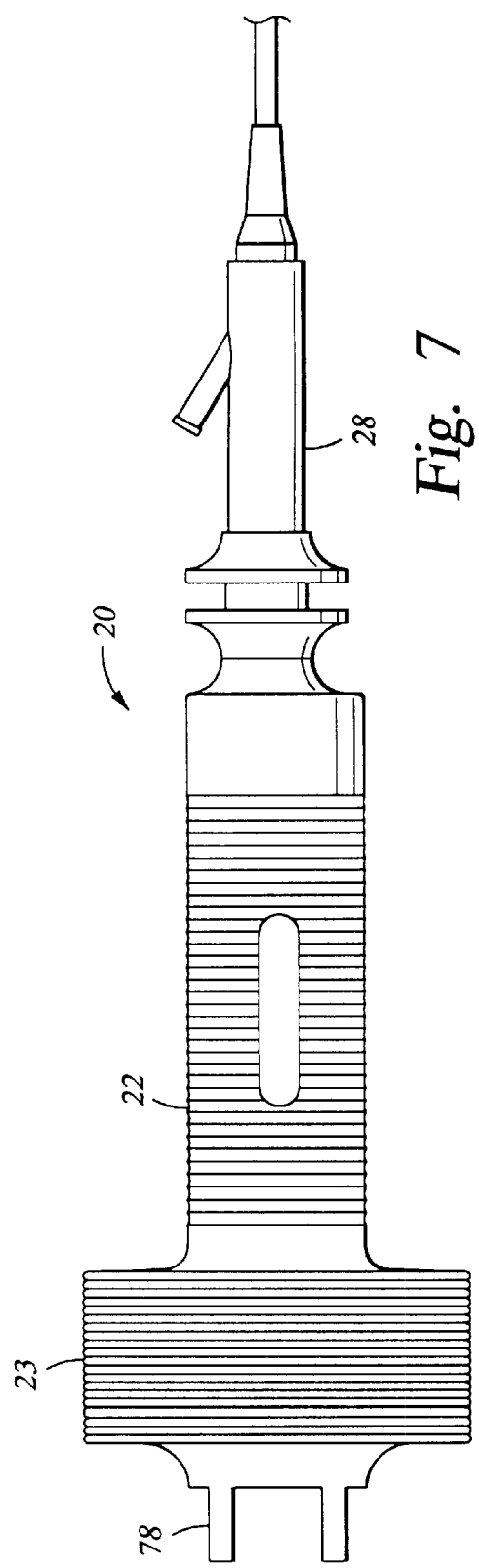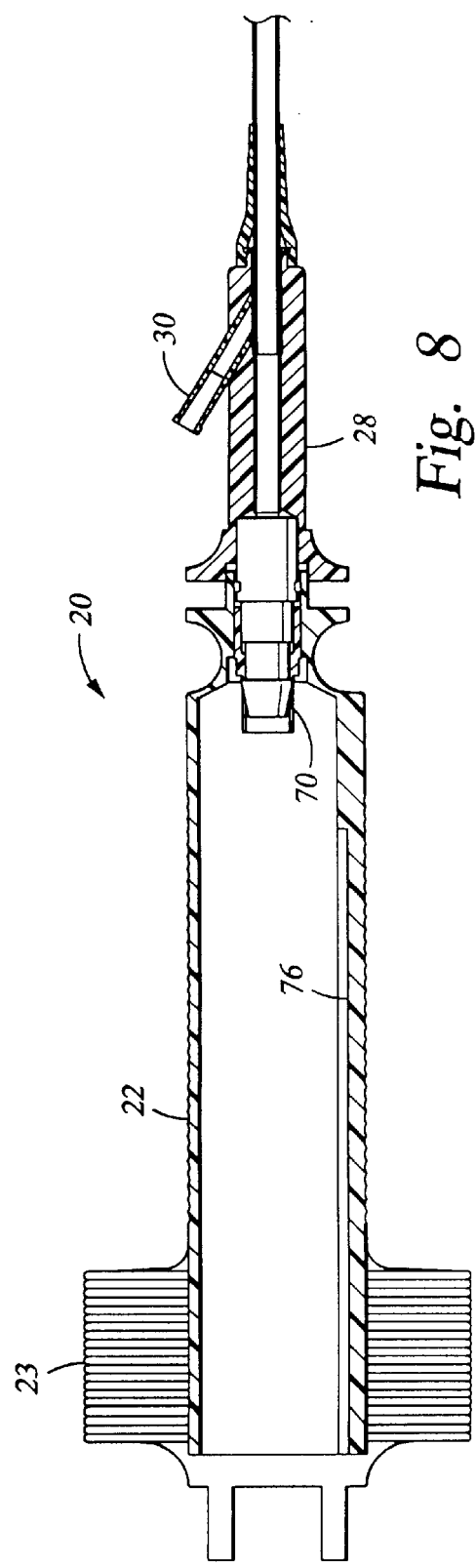

CRYOSURGICAL PROBE WITH SHEATH

CROSS REFERENCE TO RELATED APPLICATIONS

This is a continuation patent application of U.S. Pat. Application Ser. No. 08/774,148,filed on Dec. 26 1996, now U.S. Pat. No. 5,910,104 and entitled "Cryosurgical Probe with Disposable Sheath."

FEDERALLY SPONSORED RESEARCH OR DEVELOPMENT

Not Applicable.

BACKGROUND OF THE INVENTION

The present invention is in the field of cryosurgical probes used for freezing and thereby destroying biological tissues. More specifically, the present invention is useful in the field of cryosurgical probes which are cooled by a closed loop Joule-Thomson refrigeration system.

A Joule-Thomson refrigeration system operates by expanding a high pressure gas through an expansion element which incorporates some sort of a flow restriction. The flow restriction might be a small orifice, a narrow capillary tube, or some other sort of restricted passageway. Typically, the refrigeration system includes a source of high pressure gas, a heat exchanger, an expansion element, a heat transfer element, and various tubes or conduits to conduct the gas from one component to another. The high pressure gas passes through the heat exchanger to lower the gas temperature somewhat, then the gas temperature is further lowered in the expansion element, as isenthalpic expansion occurs. The expanded, cooled gas is exposed to the heat transfer element, where the gas absorbs heat which has been transferred from the environment. The operation of a Joule-Thomson refrigeration system can be severely affected by contaminants in the gas, such as water, oil, or particulates. Any such contaminant can easily block the flow restriction in the expansion element, because the flow restriction is typically very small.

Water and oil are particularly detrimental contaminants, because they will selectively collect at the flow restriction, where the majority of the cooling occurs. As the gas expands and cools, the temperature of entrained water and oil also lowers, resulting in the freezing or solidification of the water and oil. This solidification occurs exactly at the flow restriction, because that is where the cooling actually occurs. Water and oil, at least in trace amounts, are often found in ambient air, and they can consequently be introduced into the refrigeration system if any system joints are broken or any system parts are replaced.

Most Joule-Thomson systems are open loop, meaning that the gas is exhausted to the atmosphere after expansion and heat absorption. The source of the high pressure gas in such a system is usually a high pressure gas cylinder. As use proceeds, the amount of gas in the cylinder is depleted. An open loop system such as this can tolerate a certain amount of contamination, because the contaminants are exhausted from the system to the environment along with the gas, during use. If any contamination is introduced into the system during the replacement of parts, or when system joints are broken for other reasons, the contamination is largely flushed out as the gas is subsequently exhausted.

However, it is possible to operate a closed loop Joule-Thomson system, meaning that the gas is repressurized and circulated after expansion. After expansion in the expansion element, exposure to the heat transfer element, and absorption of heat, the low pressure gas is returned to a compressor which can be used to repressurize the gas. The repressurized gas is then circulated back through the heat exchanger and the expansion element. None of the gas is exhausted from the system. Therefore, any contaminants which enter the system are collected in the system, where they accumulate over a period of time. The level of contamination can eventually build up to a level where solidification of the water and oil will plug the expansion element. A method and apparatus have been developed for operating a micro-miniature mixed-gas Joule-Thomson refrigeration system, as disclosed in U.S. patent application Ser. No. 08/542,123, filed Oct. 10,1995, and U.S. patent application Ser. No. 08/698,044, filed Aug. 15,1996, which are incorporated herein for reference. If such a mixed-gas is used, especially in a miniature or micro-miniature refrigeration system, the introduction of air into the system alters the gas mixture ratios, and it can significantly detract from the cooling performance of the gas mixture.

For these reasons, closed loop Joule-Thomson systems are often permanently sealed, to prevent the introduction of contaminants. Replacement of parts, or other breaking of system joints, is not possible in a permanently sealed system. Some systems use self sealing couplings, which automatically close the system when they are broken apart. This automatic sealing limits the amount of leakage and contamination, but some contamination still occurs. Typically, the couplings used in a closed loop system are threaded fittings which are not designed for repetitive disconnection.

The contamination problem becomes more complicated in a closed loop mixed-gas Joule-Thomson refrigeration system which is used in a surgical device, such as a cryosurgical probe. Such a device will typically have a compressor hooked to the probe, with the probe consisting essentially of a handle, a cannula, and a cold tip. The heat exchanger is typically located in the handle, and the expansion element is typically located in the cold tip. The probe cannula or cold tip must be interchangeable with various shapes, such as flat, cylindrical, or sharp edged, to perform different functions. Further, the cold tip must be capable of being sterilized for use in a surgical application, to allow repeated use of the system on different patients.

Known cryosurgical probes are open loop systems for this reason. In an open loop system, the cannula or cold tip can be removed and sterilized or discarded. Introduction of contaminants into the refrigeration system during removal and replacement of the cannula or cold tip is not a significant problem in an open loop system, since the contaminants can be flushed from the system during exhaust of the gas. Open loop systems are wasteful and expensive to operate, because of the necessity of continually replacing the gas. Also, exhaust of the gas to the environment is not always environmentally safe. Closed loop systems are more economical and environmentally safe. If a known closed loop system were used in a surgical application, removal and replacement of the cannula or cold tip for sterilization purposes would introduce contaminants into the system, ultimately resulting in blockage of the expansion element. A closed loop surgical system could theoretically be provided with self sealing couplings, but contamination would still build up over a period of time. Further, self sealing couplings incorporate O-rings and precision parts. Sterilization of the cannula or cold tip would inevitably expose the O-rings and precision parts to high temperatures and harsh chemicals, ultimately resulting in degradation of the sealing ability of the couplings.

Use of disposable replacement cannulas or cold tips would not solve this dilemma. First, even if the replaceable parts are discarded and replaced with new, sterile parts, repetitive disconnections are required, ultimately resulting in the buildup of contaminants. Second, most disposable parts are constructed of plastic, for reasons of economy. Plastics typically contain trace amounts of water. If a plastic part is exposed to the gas in a refrigeration system, the water can eventually leech out of the plastic and contaminate the gas in the system. Third, self sealing fittings typically add size, weight, and significant cost to a device, making them undesirable for use in a disposable device. Fourth, each time a disposable element, such as a cannula or cold tip, is discarded, the refrigerant gas contained within the disposable element is lost. This requires replacement of the gas to avoid degradation of the cooling performance of the system. Evacuation of gas from the disposable component, or use of replacement components precharged with gas, would significantly add to the complexity and cost of the system.

Further, a typical cryosurgical probe will have one or more auxiliary instruments near the cold tip, for use in conjunction with the cold tip, such as temperature sensors, heaters, ultrasound transducers, optical elements, and fluid ports for irrigation and aspiration. If a reusable probe is employed, repetitive sterilization of these auxiliary instruments can degrade their performance. The ideal practice would be to incorporate these auxiliary instruments into a disposable element.

Finally, it is desirable to insulate the shaft of a cryosurgical probe, to prevent freezing of tissue at undesired sites along the probe when the probe is inserted into a body cavity or organ. One effective means of insulation would be to provide a vacuum space along the probe shaft. However, the level of the vacuum maintained in such a space can degrade over time, because of the outgassing of metals, plastics, and braze joints. This outgassing increases during sterilization procedures in which heat is applied to the probe. Therefore, it would be desirable to incorporate the vacuum insulation space into a disposable element. The disposable element would only be sterilized once, and the disposable element can then be economically discarded, minimizing the amount of vacuum degradation.

BRIEF SUMMARY OF THE INVENTION

The present invention is a sheath for use on a closed loop Joule-Thomson cryosurgical probe, and the combination of the sheath and the closed loop probe. The sheath is sufficiently flexible to be slipped over the probe, thereby separating the probe from the environment and allowing use of the probe in a surgical application. The sheath has a grip which fits snugly over the handle of the cryosurgical probe, and an extendible shroud attached to the proximal end of the grip. The shroud can be longitudinally extended to cover the refrigerant tubing and instrumentation cables which are attached to the handle, thereby providing a sterile barrier for these components.

The sheath also has a hollow multi-lumen catheter attached to the distal portion of the grip, with at least one lumen being shaped and sized to fit snugly over the cannula of the cryosurgical probe. The catheter is not thermally conductive, so it assists in preventing transfer of heat from the ambient to the gas mixture, and preventing the freezing of tissues at undesired locations along the catheter. Thermal conductivity of the catheter can be reduced by the provision of insulation, such as a vacuum space, along the sides of the catheter. A thermally conductive segment is attached to the distal end of the multi-lumen catheter, in the form of a metal cap or tip. The metal tip can be round, flat, sharp, or any other shape suitable for the cryosurgical operation being performed. The thermally conductive cap or tip fits snugly over the cold tip on the probe, and it efficiently transfers heat from the target tissue to the cold tip, which in turn transfers heat to the expanded gas mixture. Various forms of auxiliary instrumentation can be mounted on the catheter or conductive tip, such as a temperature sensor, a heater, a tissue impedance measuring component, an ultrasonic transducer, or an optical element of a viewing, illumination, or laser system. Connections between the instrumentation near the distal end of the catheter and the probe are made via a plurality of lumens passing longitudinally through the wall of the catheter. Fluid passageways can also be included in the catheter, and they can be connected to fluid sources connected to, or mounted on the sheath, such as a saline reservoir mounted on the grip of the sheath.

The novel features of this invention, as well as the invention itself, will be best understood from the attached drawings, taken along with the following description, in which similar reference characters refer to similar parts, and in which:

BRIEF DESCRIPTION OF THE DRAWINGS

FIG. 1 is an elevation view of a cryosurgical probe of the type which might be used in the present invention;

FIG. 2A is an elevation view of a sheath according to the present invention;

FIG. 2B is an elevation view of an alternative embodiment of the sheath according to the present invention;

FIG. 2C is a distal end view of the alternative embodiment of the sheath shown in FIG. 2B;

FIG. 3 is an elevation view of a sheath in place over a cryosurgical probe, according to the present invention;

FIG. 4 is a schematic view of a cryosurgical probe as shown in FIG. 1;

FIG. 7 is an elevation view of the proximal portion of the sheath of FIG. 1, with the shroud furled;

FIG. 8 is a section view of the proximal portion of the sheath of FIG. 7, with the shroud furled;

DETAILED DESCRIPTION OF THE INVENTION

Figure 5:
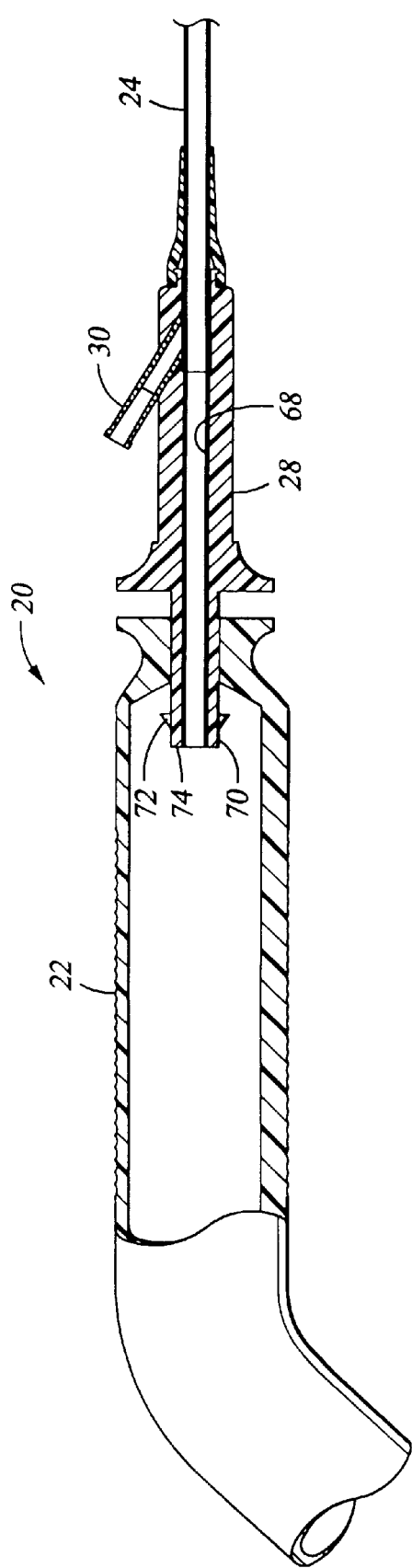
FIG. 5 is a section view of the proximal portion of the sheath as shown in FIG. 2A.

The present invention addresses the use of a sheath on a cryosurgical probe which operates on a closed loop mixed gas Joule-Thomson refrigeration system. Such a cryosurgical probe 10 is shown in FIG. 1. The probe 10 consists mainly of a handle 12, a hollow tubular cannula 14, and a cold tip 16. The handle 12 can be metallic, to facilitate effective sealing. The handle can have end caps vacuum brazed to the handle cylinder, to hold a vacuum inside the handle 12, thereby providing insulation. Alternatively, the handle 12 could be packed with insulating material, such as aerogel. Several components of the refrigeration system, such as a heat exchanger, can be housed within the handle 12, along with various auxiliary instrumentation to support items such as temperature sensors, heaters, illumination optics, viewing optics, laser optics, and ultrasonic transducers. An umbilical cord 18 extending from the proximal portion of the handle 12 can contain tubing for the refrigeration system, power cables for the electrical components, or fiber optical cables to support the illumination, viewing, and laser components.

Other components of the refrigeration system, such as a high pressure conduit to transport a high pressure gas mixture from the probe handle 12 to the cold tip 16, and a low pressure conduit to return the expanded gas mixture from the cold tip 16 to the probe handle 12, can be housed in the hollow cannula 14. Still other components of the refrigeration system, such as a Joule-Thomson expansion element, can be housed in the cold tip 16. The hollow cannula 14 is usually designed to minimize heat transfer from the surrounding tissues to the cryogenic gas mixture. It can be formed of a thermally resistive material, such as a rigid plastic, or it can be formed of a metal, with insulation applied internally or externally to inhibit heat transfer. The cannula 14 can be a rigid tube as shown, or it can be more flexible and shaped differently, depending upon the application. The cold tip 16 is a heat transfer element designed to maximize heat transfer from the target tissues to the expanded gas mixture. It can be formed of a thermally conductive material, such as a metal, preferably silver. The cold tip 16 can be a cap shaped element on the distal end of the cannula 14 as shown, or it can have another shape and be placed elsewhere on the cannula 14, depending upon the application. A plurality of grooves 17 are formed in the cold tip 16 to allow the flow of thermal grease as the cold tip 16 is fitted inside the disposable sheath. Since the cryosurgical probe 10 is used with a closed loop refrigeration system, it will necessarily be sealed to prevent contamination. It may have breakable joints which allow for replacement of parts, but any such joints will necessarily have sealing components which are not suitable for normal sterilization procedures.

FIG. 2A shows a sheath 20 for disposition over the probe 10, to allow use of the probe 10 in a protected environment without degradation of the effectiveness of the probe 10. Optionally, the sheath 20 can be made of materials that are sterilized easily, and it can be constructed cheaply enough to be disposable. The sheath 20 includes a grip 22 which fits over the probe handle 12, preferably with corrugations or other surface features to provide a secure feel for the surgeon. An extendible shroud 23 is attached to or formed on the proximal portion of the grip 22. The shroud 23 is shown in FIG. 2A in the unfurled, or extended, condition, covering the umbilical cord 18 and the proximal portion of the probe handle 12. The grip 22 and the shroud 23 are constructed of a thermally non-conductive material, such as a plastic. They should have some flexibility to allow them to fit over the probe handle 12 and the umbilical cord 18. The sheath 20 also includes a hollow tubular catheter 24 extending distally. The hollow catheter 24 is shaped and sized to cover the cannula portion 14 of the cryosurgical probe 10, preferably fitting tightly over the probe cannula 14 to avoid interference with use of the probe 10 in a surgical environment. The hollow catheter 24 is constructed of a thermally resistive material, such as a plastic, to further inhibit heat transfer from the surrounding tissues to the probe cannula 14.

Attached to the distal end of the hollow catheter 24 is a thermally conductive segment, such as a cap shaped tip 26. The sheath tip 26 is shaped and sized to fit snugly over the probe cold tip 16, to maximize the transfer of heat through the sheath tip 26 to the probe cold tip 16. The sheath tip 26 can be a cap shaped element on the distal end of the catheter 24 as shown, or it can be a thermally conductive segment shaped and located otherwise, to match the configuration and location of the probe cold tip 16. The thermally conductive segment of the sheath, such as sheath tip 26, must be constructed of a material which will readily transfer heat, such as a metal. All of the components of the sheath 20 are attached together in a sealing relationship, so that when the sheath 20 is sterile, it covers the probe 10 in a protective envelope, rendering the probe 10 suitable for use in a surgical environment. Various auxiliary instruments for use in conjunction with cryosurgery can be mounted in the hollow catheter 24 or the sheath tip 26, as will be explained below. These instruments can include temperature sensors, heaters, viewing optics, illumination optics, laser optics, and ultrasonic transducers. Controls for operating these instruments, or devices for displaying readings from these instruments, can be mounted in the probe handle 12 or elsewhere, for ease of observation and use by the surgeon. Connections between the instrumentation near the sheath tip 26 and the control devices in the probe handle 12 or proximal to the handle 12 can be carried by the hollow catheter 24 as will be explained.

The sheath 20 can also include a substantially rigid connector body 28, which performs several functions. The connector body 28 provides a means for connecting the hollow catheter 24 to the grip 22. It can also provide a means for latching the sheath 20 to the probe 10. Further, the connector body 28 can provide a mounting location for connectors, such as electrical contacts or optical elements, to connect auxiliary instrumentation near the sheath tip 26 to the probe handle 12.

Finally, the connector body 28 can provide a mounting location for a port or fitting 30, such as a luer fitting, which can be used to provide fluid flow to or from the area adjacent the sheath tip 26. Fluid flow to the area can be required in some applications where fluid such as a saline solution must be injected into a body cavity having a small opening. An example of such an application is insertion of the probe cannula 14 into the uterus for endometrial ablation. Fluid flow to the area around the tip 26, such as a saline solution or another fluid suitable for irrigation of the area, can be provided by a syringe attached to the fitting 30. Alternatively, as shown in FIGS. 2B and 2C, a pliable saline reservoir 25 can be mounted on the grip 22 and connected to the fitting 30 by a tube 27. Squeezing or depressing the saline reservoir 25 can inject saline solution into the fitting 30. The injected fluid can be retained in the body cavity by sliding a plug (not shown) over the cannula 14 and the catheter 24 to fit snugly between the catheter 24 and the opening of the body cavity. Similarly, a balloon (not shown) can be inflated around the catheter 24 to seal against the cavity opening. Fluid flow from the area around the tip 26 can be achieved by connecting a vacuum source to the fitting 30. Fluid flow can pass between the tip area and the fitting 30 via the hollow catheter 24, as will be explained below.

FIG. 2A also shows the finger stop 32 formed on the distal portion of the sheath grip 22, and the finger slide 34 formed on the proximal portion of the connector body 28. As will be shown below, the finger slide 34 can be pulled toward the finger stop 32 to unlatch the connector body 28 from the probe handle 12.

FIG. 3 shows the combined cryosurgical instrument 40 of the present invention, consisting of the sheath 20 disposed over the probe 10 as a protective cover, having a thermally conductive segment for effectively transferring heat from the target tissue to the cold tip 16 of the probe 10. It should be noted that the shroud 23 of the sheath 20 is sufficiently flexible to stretch over the proximal end of the probe handle 12 and the umbilical cord 18.

FIG. 4 is a schematic drawing of the cryosurgical probe 10, in the style of a longitudinal section view, to illustrate the components and functions of the typical probe 10 which can be incorporated into the present invention. A high pressure gas tube 36 provides a warm high pressure gas mixture to the refrigeration components in the probe 10, and a low pressure gas tube 38 receives the cool low pressure gas mixture returning from the probe 10. The high pressure and low pressure gas tubing 36, 38 is connected to the outlet and inlet, respectively, of a gas compressor 42. The high pressure tube 36 is also connected to a high pressure passageway through a precooling heat exchanger 44, and the low pressure tube 38 is connected to a low pressure passageway through the heat exchanger 44. The heat exchanger 44 precools the warm high pressure gas mixture by heat exchange with the cool low pressure expanded gas mixture, before the high pressure gas is expanded at the cold tip 16.

A high pressure outlet 46 of the heat exchanger 44 is connected to a high pressure conduit 48 which passes through the hollow cannula 14 to the cold tip 16. At the distal end of the high pressure conduit 48 is a Joule-Thomson expansion element 50, located in, or immediately adjacent to, the cold tip 16. High pressure cryogenic gas mixture passing through the high pressure conduit 48 is isenthalpically expanded by the expansion element 50, to significantly lower the temperature of the gas mixture. The colder, low pressure gas mixture is then exposed to the cold tip 16, to cool the target tissue via the thermally conductive sheath tip 26. A separator plate 52 isolates the low pressure region of the cold tip 16 from the probe cannula 14. Low pressure gas mixture passes back through openings in the separator plate 52 to return via the probe cannula 14 to the low pressure inlet 54 of the heat exchanger 44. The flow of the low pressure gas mixture back through the cannula 14 can actually be via a low pressure conduit not shown in FIG. 4.

A female connector fitting 56 is provided in the distal portion of the probe handle 12, to provide for a mating location between the probe 10 and the sheath 20. An inwardly projecting latching flange 58 can be provided around the outer perimeter of the female connector 56. One or more connector elements 60 can be provided within the female connector 56 for mating with auxiliary instrumentation carried by the sheath 20. The connector element 60 can be an electrical contact for use with auxiliary instrumentation such as a temperature sensor, a heater, or an ultrasonic transducer. Similarly, the connector element 60 can be an optical element for use with auxiliary instrumentation such as viewing optics, illumination optics, or laser optics. The connector element 60 is connected by way of an instrumentation conductor 62 to a display or control device 64. The instrumentation conductor 62 can be an electrical conductor or an optical fiber bundle, as appropriate. Only one set of connector element 60, conductor 62 and display or control device 64 is shown, for the sake of simplicity, but it should be understood that a plurality of such systems could be used in any given cryosurgical instrument 40. Further, it should be understood that the display or control device 64 could be located remotely from the instrument 40, such as would be appropriate for a video optical viewing system. An alignment rib 66 can be formed on the perimeter of the probe handle 12, to assist in alignment of the probe handle 12 with the sheath grip 22.

Figure 6:
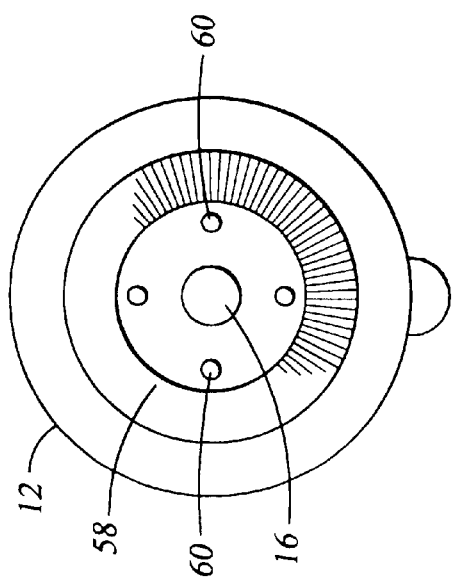
FIG. 6 is a distal end view of the cryosurgical probe as shown in FIG. 1.

FIG. 5 shows that the connector body 28 has a longitudinal bore 68 therethrough, to allow the passage of the probe cannula 14. The fitting 30 is in fluid flow communication with the bore 68, to provide fluid flow to the exterior of the hollow catheter 24, which extends into the bore 68. A male connector fitting 70 is provided on the proximal portion of the connector body 28 to mate with the female connector fitting 56 in the distal portion of the probe handle 12. A releasable latch 72 is provided on the male connector fitting 70, to engage the latching flange 58. One or more connector elements 74 are also provided on the male connector fitting 70 to engage the connector elements 60 within the female connector fitting 56 in the probe handle 12. Connection of the connector element 74 to the auxiliary instrumentation, and connection of the fluid flow path from the fitting 30 to the hollow catheter 24 are shown better in a later Figure FIG. 6 is an end view of the probe handle 12, showing the interior of the female connector fitting 56. A plurality of connector elements 60 are shown arranged in a circle within the female fitting 56.

FIG. 7 shows the sheath 20 with the shroud 23 in the furled, or contracted, condition. The sheath would normally be shipped and stored in this condition until disposition over a cryosurgical probe 10. Tabs 78 are provided on the proximal end of the shroud 23 to assist in pulling the shroud 23 over the probe handle 12 and the umbilical cord 18. FIG. 8 is a section view showing more detail of one embodiment of the sheath 20. An alignment groove 76 is shown in the inner bore of the sheath grip 22, to mate with the alignment rib 66 on the exterior of the probe handle 12. It can be seen that the connector body 28 can be constructed as a multi-piece assembly.

Figure 9:
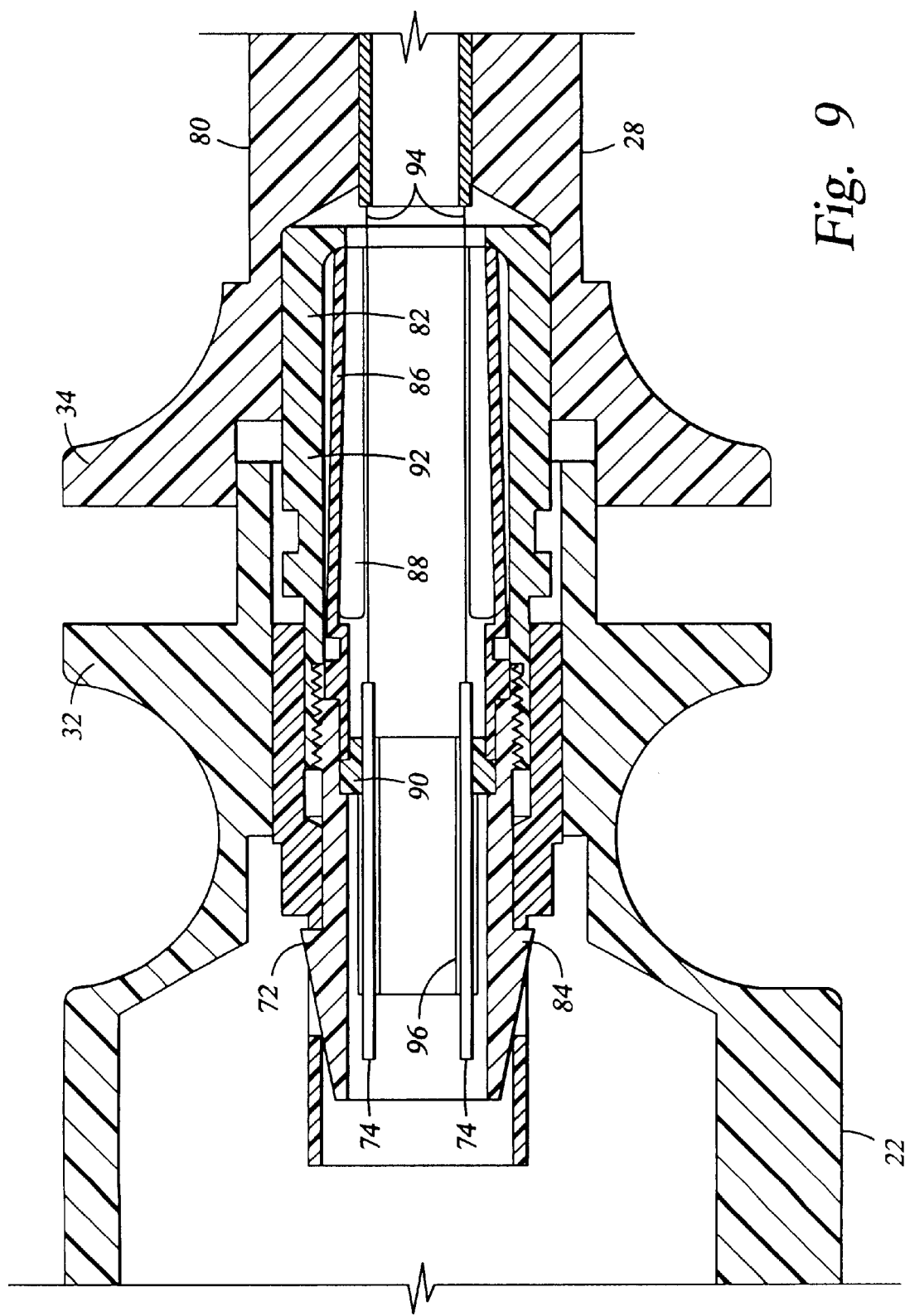
FIG. 9 is a longitudinal section view of the proximal portion of the connector body of the sheath.

FIG. 9 shows more detail of one embodiment of the connector body 28 and its connection to the sheath grip 22. The connector body 28 comprises essentially a distal section 80, an intermediate section 82, and a proximal section 84. The distal section 80 includes the finger slide 34, and the distal portion of the distal section 80 is attached to the hollow catheter 24. The intermediate section 82 is mounted within the proximal portion of the distal section 80, and it provides a means of connecting the distal section 80 to the instrumentation connectors 74 and to the releasable latch 72. The intermediate section 82 can consist of a barrel 92 as shown, threaded to the latch 72. A collet 86 is captured between the barrel 92 and the latch 72. The collet 86 is attached to a sleeve 90 which is in turn attached to a connector fixture 96. Instrumentation conductors 94 are connected to the instrumentation connectors 74. The instrumentation conductors 94 pass through or alongside the longitudinal bore 68 to the catheter 24.

Figure 10:
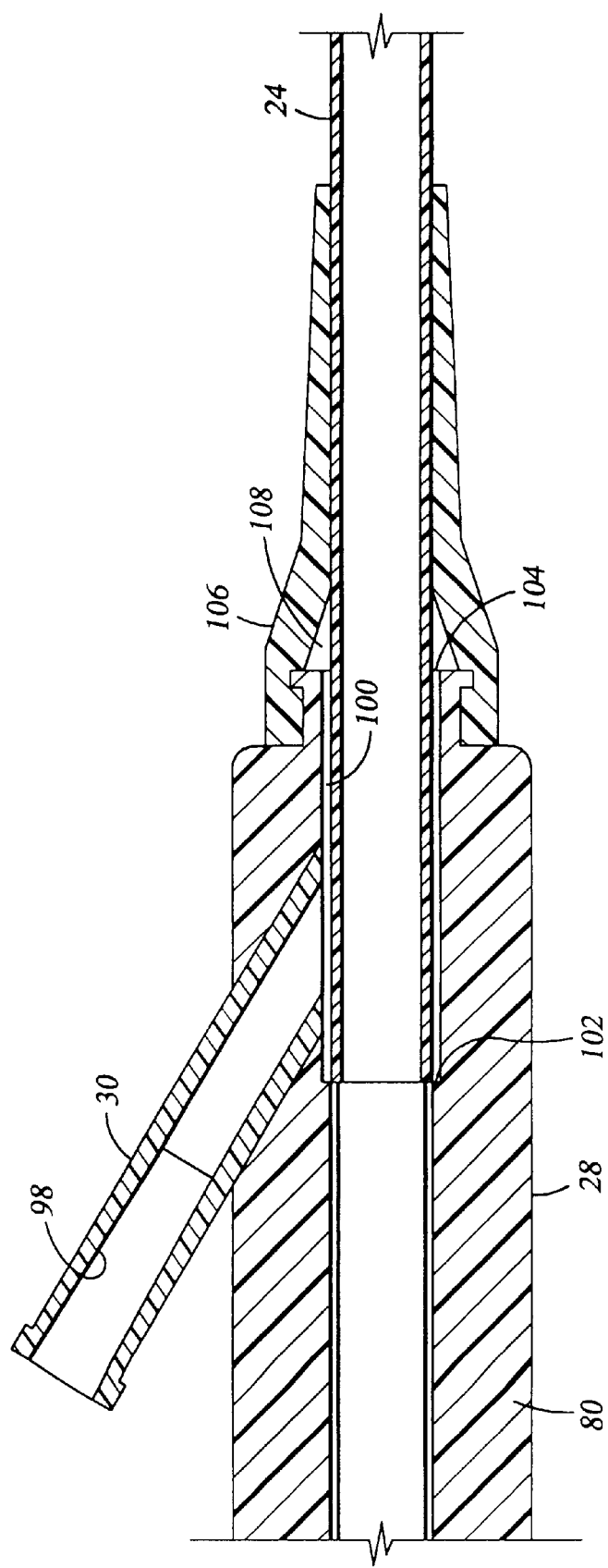
FIG. 10 is a longitudinal section view of the distal portion of the connector body of the sheath.

FIG. 10 shows more detail of one embodiment of the distal portion of the distal section 80 of the connector body 28. The distal end of the longitudinal bore 68 terminates in a fluid bore 100, which is in fluid flow communication with an internal bore 98 of the fitting 30. The proximal portion of the hollow catheter 24 extends into the fluid bore 100, with the diameter of the fluid bore 100 being larger than the outer diameter of the catheter 24. This leaves a fluid flow space surrounding the catheter 24 in the fluid bore 100. The proximal end 102 of the fluid bore 100 can be terminated by a shoulder in the longitudinal bore 68. Conversely, the proximal end 102 of the fluid bore 100 can be terminated by an epoxy seal. The probe cannula 14 can fit snugly within the longitudinal bore 68. The distal end of the connector body 28 can be fitted with a strain relief collar 106 to fasten the catheter 24 to the connector body 28. A space 108 within the collar 106 can be filled with epoxy to terminate the distal end of the fluid bore 100.

Figure 11:
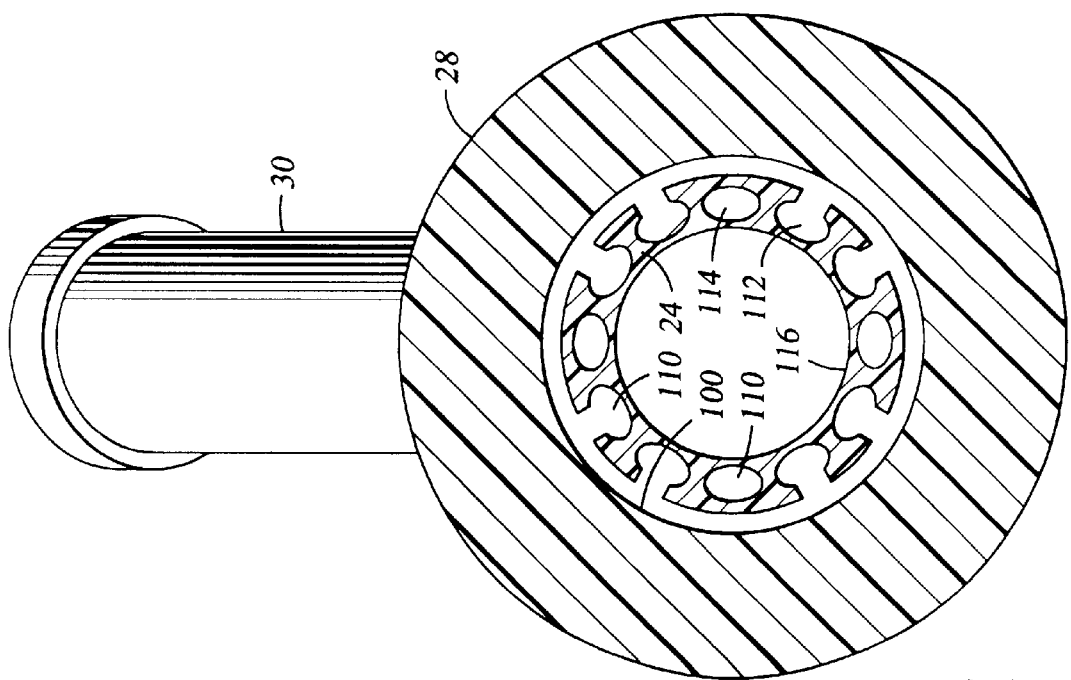
FIG. 11 is a transverse section view of the distal portion of the connector body of the sheath.

FIG. 11 shows a section view of the distal portion of the connector body 28 and the proximal portion of the hollow catheter 24. In this view, it can be seen that the catheter 24 is a multi-lumen catheter. A plurality of lumens 110 pass longitudinally through the wall of the catheter 24. Some of the lumens 110 are used to conduct fluid flow, as shown at 112, and other lumens are used to conduct auxiliary instrumentation signals, as shown at 114. Within the fluid bore 100 only, the fluid lumens 112 are open to the exterior of the catheter 24, while the fluid lumens 112 along the remainder of the length of the catheter 24 are not open to the exterior. The instrumentation lumens 114 are closed to the exterior throughout the length of the catheter 24. Since the fluid lumens 112 are open to the exterior within the fluid bore 100, fluid can flow from the fitting 30 into the wall of the catheter 24, or out of the wall of the catheter 24 to the fitting 30. A central bore 116 passes through the catheter 24 to accommodate the probe cannula 14.

Figure 12A:
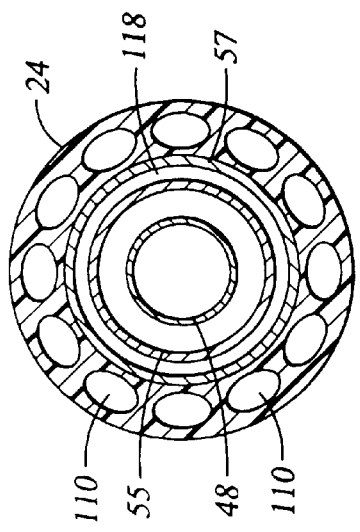
FIG. 12A is a transverse section view of the catheter of the sheath installed on the cannula of the cryosurgical probe.

FIG. 12A shows a transverse section view of the catheter 24 and the probe cannula 14, forward of the connector body 28. The cannula 14 incorporates a set of three coaxial stainless steel tubes 48,55,57, with the outer tube 57 fitting substantially snugly within the catheter 24. It can be seen that a vacuum or insulation space 118 is formed between the outer tube 57 and a low pressure conduit 55. The low pressure conduit 55 leads to the low pressure inlet 54 of the heat exchanger 44. The high pressure conduit 48 lies within the low pressure conduit 55.

Figure 12B:
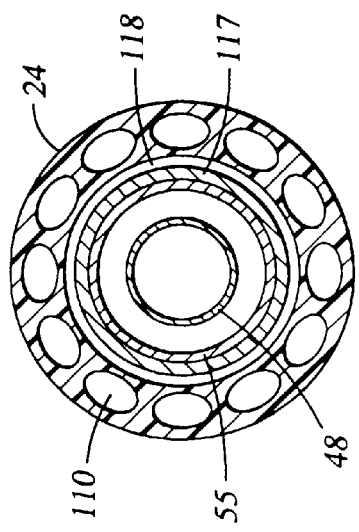
FIG. 12B is a transverse section view of an alternate embodiment the catheter of the sheath, incorporating a vacuum jacket, installed on the cannula of the cryosurgical probe.

FIG. 12B shows a transverse section view of an alternate embodiment of the catheter 24 and the probe cannula 14, forward of the connector body 28. The cannula 14 incorporates a set of two coaxial stainless steel tubes 48,55, with the outer tube 55 fitting substantially snugly within an inner tube 117 in the catheter 24. It can be seen that a vacuum jacket or insulation space 118 is formed within the catheter 24, between the inner tube 117 and the catheter 24. Here as before, the low pressure conduit 55 leads to the low pressure inlet 54 of the heat exchanger 44. The high pressure conduit 48 lies within the low pressure conduit 55.

Figure 13:
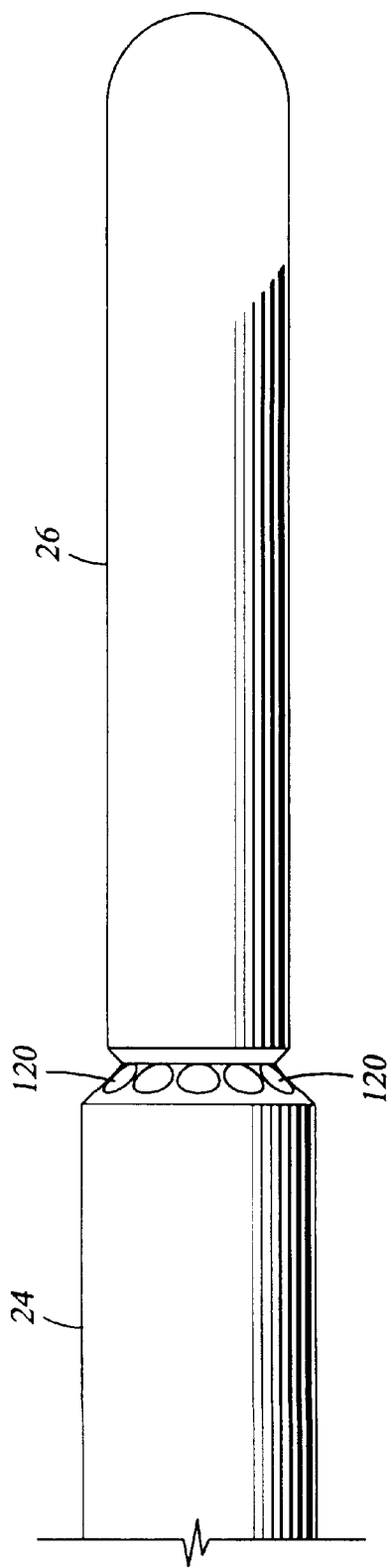
FIG. 13 is an elevation view of the distal end of the catheter of the sheath.

FIG. 13 shows an elevation view of the distal end of the hollow catheter 24 and the sheath tip 26. A plurality of ports 120 in the lumens 110 are formed in the distal end of the catheter 24. Some of the ports 120 are for fluid flow to or from the area adjacent the sheath tip 26. Other ports 120 are for optical elements to support viewing, illumination, or laser systems. Still other ports 120 could be used as connection terminals for electrical connection to a temperature sensor, heater, or ultrasonic transducer in the sheath tip 26.

Figure 14:
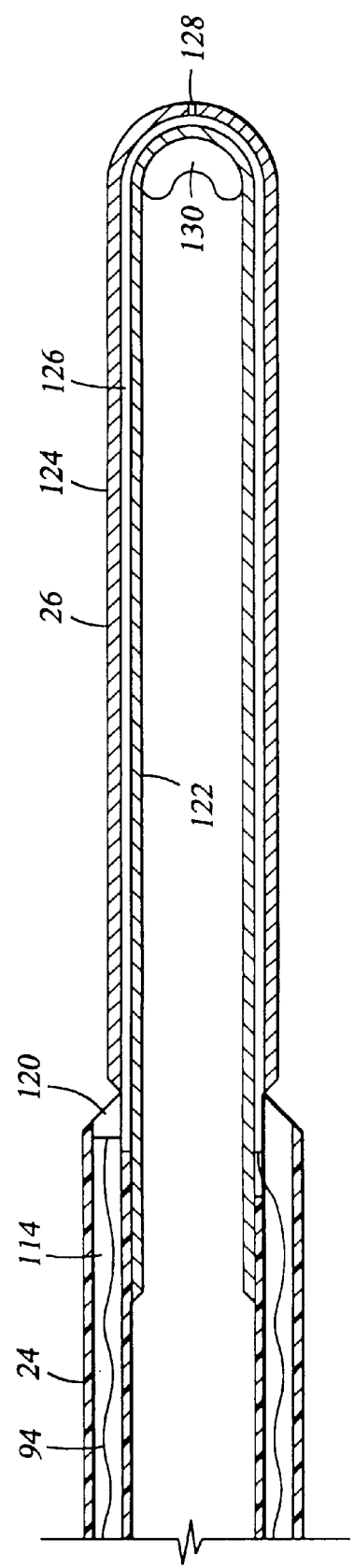
FIG. 14 is a longitudinal section view of the distal end of the catheter of the sheath.

FIG. 14 shows a longitudinal section of the distal portion of the catheter 24 and the sheath tip 26. The auxiliary instrumentation conductor 94 passes through a lumen 114 to the distal end of the catheter 24, at which point it connects to an optical element in the port 120, or to an auxiliary instrument 126 in the sheath tip 26. The auxiliary instrument 126 could be a temperature sensor, a heater, a tissue impedance measuring component, or an integrated component for performing two or more of the temperature sensing, impedance measuring, and heating functions. For example, the instrument 126 could be a combination heater and resistance temperature detector (RTD) constructed of foil laminated between very thin (0.003 in.) sheets of polyimide film. Further, the auxiliary instrument could be an ultrasonic transducer. Those auxiliary instruments 126 which are in the sheath tip 26 can be sandwiched between an inner thermally conductive layer 122 and an outer thermally conductive layer 124. The inner conductive layer 122 can be made of copper, and the outer conductive layer 124 can be made of stainless steel. If desired, epoxy can be injected between the instrument 126 and the conductive layers 122, 124. An epoxy bleed hole 128 in the outer layer 124 is provided for this purpose. If insulating layers are placed between the instrument 126 and the inner and outer layers 122, 124, the insulating layers must be sufficiently thin to allow heat transfer therethrough. A thermally conducting grease 130 can be provided within the sheath tip 26 to maximize the thermal contact between the probe tip 16 and the sheath tip 26.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

We claim:

1. A sheath for use as a removable cover for a cryosurgical probe, said sheath comprising:
  a hollow grip removably attachable over a handle portion of a cryosurgical probe;
  a connector body attached to said hollow grip;
  a tubular passageway through said connector body for receiving a cannula portion of a cryosurgical probe therethrough;
  a thermally resistive catheter attached to said connector body, said catheter being removably disposable over a cannula portion of a cryosurgical probe; and
  a thermally conductive segment attached to said catheter, said conductive segment being removably disposable over, and in thermal contact with, a heat transfer portion of a cryosurgical probe.

2. A sheath for use as a removable cover for a cryosurgical probe, said sheath comprising:
  a hollow grip removably attachable over a handle portion of a cryosurgical probe;
  a longitudinally collapsible shroud attached to a proximal end of said hollow grip for extending proximally from said grip, to shroud cryogenic tubing attached to a cryosurgical probe;
  a connector body attached to a distal end of said hollow grip;
  a latch formed on a proximal portion of said connector body for releasably attaching said connector body to a cryosurgical probe;
  a tubular passageway through said connector body for receiving a cannula portion of a cryosurgical probe therethrough;
  a thermally resistive multi-lumen catheter attached to said connector body, said catheter having a first lumen for receiving a cannula portion of a cryosurgical probe, said catheter having a second lumen for receiving an instrumentation conductor, said catheter having a third lumen for passage of a fluid; and
  a thermally conductive tip attached to a distal end of said catheter, said conductive tip being removably disposable over, and in thermal contact with, a cold tip portion of a cryosurgical probe.

3. A cryosurgical instrument, comprising:

a probe handle;

a probe cannula attached to said probe handle;

a heat transfer element attached to said probe cannula;

a closed loop, mixed gas, Joule-Thomson cooling system providing a gas mixture at a desired temperature adjacent said heat transfer element;

a hollow grip removably attachable over said probe handle;

a thermally resistive catheter attached to said hollow grip, said catheter being removably disposable over said probe cannula; and a thermally conductive segment attached to said catheter, said conductive segment being removably disposable over, and in thermal contact with, said heat transfer element.

4. A cryosurgical instrument, comprising:

a probe handle;

a probe cannula attached to a distal end of said probe handle;

a cold tip attached to a distal end of said probe cannula;

a closed loop, mixed gas, Joule-Thomson cooling system, comprising:
  at least one compressor for compressing and circulating a gas mixture;
  at least one heat exchanger in said probe handle, said heat exchanger receiving said compressed gas mixture from said at least one compressor; and
  a Joule-Thomson expansion element adjacent said cold tip, said expansion element receiving said compressed, pre-cooled gas mixture from said at least one heat exchanger;

a hollow grip removably attachable over said probe handle;

a thermally resistive multi-lumen catheter attached to said hollow grip, said catheter being removably disposable over said probe cannula; and a thermally conductive tip attached to said catheter, said conductive tip being removably disposable over, and in thermal contact with, said cold tip on said probe.

5. A sheath for use as a removable cover for a cryosurgical probe, said sheath comprising:

a hollow grip removably attachable over a handle portion of a cryosurgical probe;

a catheter attached to said hollow grip, said catheter being removably disposable over a cannula portion of a cryosurgical probe;

a thermally conductive segment attached to said catheter, said conductive segment being removably disposable over a heat transfer portion of a cryosurgical probe; and a thermally conductive medium within said thermally conductive segment, to insure heat transfer between the heat transfer portion of the cryosurgical probe and said thermally conductive segment.

6. A cryosurgical instrument, comprising:

a probe cannula;

a heat transfer element attached to said probe cannula;

a cooling system providing a gas mixture at a desired temperature adjacent said probe heat transfer element;

a catheter removably disposable over said probe cannula;

a thermally conductive segment attached to said catheter, said conductive segment of said catheter being removably disposable over said heat transfer element of said probe; and a thermally conductive medium within said thermally conductive segment of said catheter, between said heat transfer element of said probe and said thermally conductive segment of said catheter, to insure heat transfer from said thermally conductive segment of said catheter to said heat transfer element of said probe.

7. A sheath for use as a removable cover for a cryosurgical probe, said sheath comprising:

a hollow grip removably attachable over a handle portion of a cryosurgical probe;

a catheter attached to said hollow grip, said catheter being removably disposable over a cannula portion of a cryosurgical probe; and a thermally conductive segment attached to said catheter, said conductive segment being removably disposable over, and in thermal contact with, a heat transfer portion of a cryosurgical probe.

8. A cryosurgery preparatory method, comprising:

providing a cryosurgical probe having a heat transfer element mounted thereon;

providing a thermally conductive cover;

inserting said probe heat transfer element into said conductive cover; and placing a thermally conductive medium between said probe heat transfer element and said conductive cover, to insure heat transfer from said conductive cover to said probe heat transfer element.

9. A cryosurgery preparatory method, comprising:

providing a cryosurgical probe having a heat transfer element mounted thereon;

providing a catheter having a thermally conductive segment mounted thereon;

inserting said probe into said catheter, thereby disposing said catheter conductive segment over said probe heat transfer element; and placing a thermally conductive medium between said probe heat transfer element and said catheter conductive segment, to insure heat transfer from said catheter conductive segment to said probe heat transfer element.

10. A cryosurgical instrument, comprising:

a probe handle;

a probe cannula attached to said probe handle;

a heat transfer element attached to said probe cannula;

a cooling system providing a gas mixture at a desired temperature adjacent said heat transfer element of said probe;

a hollow grip removably attachable over said probe handle;

a catheter attached to said hollow grip, said catheter being removably disposable over said probe cannula;

a thermally conductive segment attached to said catheter, said conductive segment of said catheter being removably disposable over said heat transfer element of said probe; and a thermally conductive medium between said heat transfer element of said probe and said thermally conductive segment of said catheter, to insure heat transfer from said thermally conductive segment of said catheter to said heat transfer element of said probe.

11. A cryosurgery preparatory method, comprising:

providing a cryosurgical probe having a handle attached thereto, said probe having a heat transfer element mounted thereon;

providing a catheter having a hollow grip attached thereto, said catheter having a thermally conductive segment mounted thereon;

inserting said probe into said catheter, thereby disposing said hollow catheter grip over said probe handle, and thereby disposing said catheter conductive segment over said probe heat transfer element; and placing a thermally conductive medium between said probe heat transfer element and said catheter conductive segment, to insure heat transfer from said catheter conductive segment to said probe heat transfer element.

* * * * *